United States Patent
Krimsky

(10) Patent No.: US 11,172,933 B2
(45) Date of Patent: Nov. 16, 2021

(54) METHODS AND DEVICES FOR ALTERING LUNG VOLUME

(71) Applicant: Covidien LP, Mansfield, MA (US)

(72) Inventor: William S. Krimsky, Forest Hill, MD (US)

(73) Assignee: Covidien LP, Mansfield, MA (US)

( * ) Notice: Subject to any disclaimer, the term of this patent is extended or adjusted under 35 U.S.C. 154(b) by 183 days.

(21) Appl. No.: 16/018,484

(22) Filed: Jun. 26, 2018

(65) Prior Publication Data

US 2019/0059903 A1 Feb. 28, 2019

Related U.S. Application Data

(60) Provisional application No. 62/551,332, filed on Aug. 29, 2017.

(51) Int. Cl.
| | |
|---|---|
| *A61B 17/12* | (2006.01) |
| *A61B 1/267* | (2006.01) |
| *A61L 31/14* | (2006.01) |
| *A61L 31/08* | (2006.01) |
| *A61B 5/08* | (2006.01) |
| *A61B 17/00* | (2006.01) |

(Continued)

(52) U.S. Cl.
CPC ........ *A61B 17/1214* (2013.01); *A61B 1/2676* (2013.01); *A61B 17/1215* (2013.01); *A61B 17/12031* (2013.01); *A61B 17/12036* (2013.01); *A61B 17/12104* (2013.01); *A61B 17/12145* (2013.01); *A61L 31/08* (2013.01); *A61L 31/14* (2013.01); *A61L 31/148* (2013.01);
(Continued)

(58) Field of Classification Search
CPC ........ A61B 17/12031; A61B 17/12036; A61B 17/12104; A61B 17/1214; A61B 17/12145; A61B 17/1215; A61B 2017/00809; A61B 1/2676; A61F 2002/043

See application file for complete search history.

(56) References Cited

U.S. PATENT DOCUMENTS

| | | | |
|---|---|---|---|
| 2006/0093643 A1 | 5/2006 | Stenzel | |
| 2007/0142859 A1* | 6/2007 | Buiser | B05D 7/20 606/200 |

(Continued)

FOREIGN PATENT DOCUMENTS

| | | |
|---|---|---|
| CN | 104144651 A | 11/2014 |
| CN | 104582595 A | 4/2015 |

(Continued)

OTHER PUBLICATIONS

Extended European Search Report issued in corresponding Appl. No. EP 18190078.8 dated Feb. 1, 2019.

(Continued)

*Primary Examiner* — Katherine H Schwiker

(74) *Attorney, Agent, or Firm* — Carter, DeLuca & Farrell LLP

(57) ABSTRACT

A medical device and methods for altering lung volume are disclosed. The medical device includes a coil formed of a biodegradable material including a first bioabsorbable material that is configured to deactivate a portion of a lung as the coil degrades. The method includes positioning a first coil adjacent a first target within a patient and permitting the first coil to degenerate such that a first bioabsorbable material deactivates a first portion of a lung. The first coil is formed of a biodegradable material and includes the first bioabsorbable material.

14 Claims, 8 Drawing Sheets

(51) Int. Cl.
*A61F 2/04* (2013.01)
*A61B 34/20* (2016.01)
(52) U.S. Cl.
CPC ....... *A61B 5/08* (2013.01); *A61B 2017/00004* (2013.01); *A61B 2017/00411* (2013.01); *A61B 2017/00809* (2013.01); *A61B 2017/00884* (2013.01); *A61B 2017/00893* (2013.01); *A61B 2017/00964* (2013.01); *A61B 2017/00995* (2013.01); *A61B 2017/1205* (2013.01); *A61B 2034/2051* (2016.02); *A61F 2002/043* (2013.01); *A61L 2400/16* (2013.01); *A61L 2420/08* (2013.01)

(56) References Cited

U.S. PATENT DOCUMENTS

| | | | |
|---|---|---|---|
| 2009/0076622 A1* | 3/2009 | Thompson | A61B 5/06 623/23.65 |
| 2012/0253369 A1* | 10/2012 | Morsi | A61B 17/12022 606/158 |
| 2014/0180395 A1 | 6/2014 | Wu et al. | |
| 2014/0371705 A1 | 12/2014 | Thompson et al. | |
| 2016/0000302 A1 | 1/2016 | Brown et al. | |
| 2016/0135984 A1 | 5/2016 | Rudakov et al. | |
| 2018/0132856 A1* | 5/2018 | Wierzbicki | A61B 17/12031 |

FOREIGN PATENT DOCUMENTS

| | | |
|---|---|---|
| WO | 2009082479 A2 | 7/2009 |
| WO | 2010030691 A1 | 3/2010 |

OTHER PUBLICATIONS

Office Action issued in corresponding Chinese Appl. No. CN201810994748.6 dated Sep. 22, 2020 (8 pages) including English language machine translation retrieved from the Global Dossier (8 pages).

* cited by examiner

METHODS AND DEVICES FOR ALTERING LUNG VOLUME

CROSS REFERENCE TO RELATED APPLICATION

The present application claims the benefit of and priority to U.S. Provisional Application Ser. No. 62/551,332, filed on Aug. 29, 2017 the entire contents of which are incorporated herein by reference.

BACKGROUND

1. Technical Field

The present disclosure relates to methods and devices for altering lung volume and, more specifically, to methods and devices for non-surgically altering lung volume.

2. Discussion of Related Art

Surgical procedures have been used to alter lung volume of patients with various forms of chronic obstructive pulmonary disease (COPD), e.g., emphysema. Altering lung volume can include deactivating portions of a lung to reduce lung volume.

It has been shown that deactivating diseased portions of a lung can be beneficial for a patient suffering from COPD and other lung diseases. Surgery is typically used to deactivate one or more portions of a lung. However, it can be difficult to determine the extent or which portions of the lung to deactivate before a surgical procedure. Thus, multiple surgeries may be required to deactivate the required portions of a lung. Further, surgery is typically limited to specific anatomic distributions whereas the actual disease process is more of distributed phenomena which makes it more difficult to perform targeted interventions. Moreover, each surgical procedure in a lung can create complications for a patient.

One method for deactivating diseased portions of a lung is to implant one or more metal coils within a lung that are configured to transition from a linear configuration to a coiled configuration to decrease the volume of a portion of a lung. After the volume of the lung is reduced, the coil remains within the lung. As the lung performs pulmonary functions, the lung and thus, the metal coils are in constant contact with the external environment. The exposure to the metal coils within the lung to the external environment may increase infections, may cause inflammation, may result in an increase in bleeding as a consequence of the devices continued and ongoing proximity to the vasculature, and may reduce or prevent healing within the lung.

Accordingly, there is a need for methods and devices to non-surgically deactivate portions of a lung with a decreased rate of infection and which promote healing within the lung. Additionally or alternatively, there is a need for methods and devices to selectively deactivate portions of a lung after a single non-surgical procedure.

SUMMARY

In an aspect of the present disclosure, a medical device for altering lung volume includes a coil formed of a biodegradable material and includes a first bioabsorbable material. The first bioabsorbable material is configured to deactivate a portion of a lung as the coil degrades.

In aspects, the coil includes a core material that is formed of the biodegradable material and a first coating that is disposed over the core material. The core material may include the first bioabsorbable material impregnated in the biodegradable material. The first coating may be formed of a second bioabsorbable material that is configured to dissolve after a predetermined amount of time.

In some aspects, the coil includes a second bioabsorbable material coating the first bioabsorbable material. The second bioabsorbable material may be configured to dissolve after a predetermined amount of time. The coil may include a second coating that is disposed over the first coating. The core material may be formed of the biodegradable material. The first coating is formed of the first bioabsorbable material and the second coating may be formed of a second bioabsorbable material that is configured to dissolve after a predetermined amount of time.

In certain aspects, the biodegradable material is impregnated with a third bioabsorbable material that is configured to promote healing. The biodegradable material may be a smart material having a linear configuration and a coiled configuration. The biodegradable material may be configured to transition from the linear configuration to the coiled configuration when positioned adjacent a target within a patient. The biodegradable material may be self-biased to a coiled configuration. The coil may be configured to initiate degeneration, cease degeneration, and/or accelerate degeneration in response to energy applied to the coil from outside of the patient.

In another aspect of the present disclosure, a method of altering lung volume includes positioning a first coil adjacent a first target within a patient and permitting the first coil to degenerate such that a first bioabsorbable material deactivates a first portion of a lung. The first coil may be formed of a biodegradable material and include the first bioabsorbable material.

In aspects, permitting the first coil to degenerate occurs after a predetermined amount of time. The first coil may include a second bioabsorbable material that covers the first bioabsorbable material. The second bioabsorbable material may dissolve to define the predetermined amount of time. Positioning the first coil adjacent the first target may include inserting the first coil in a linear configuration and the first coil transitioning to a coiled configuration when positioned at the first target.

In some aspects, the method may include permitting the entire first coil to degrade within the lung. Positioning the first coil adjacent the first target may include guiding an extended working channel through airways of a patient with an electromagnetic system. The method may include positioning a second coil adjacent a second target within a patient and permitting the second coil to degenerate after a predetermined amount of time to deactivate a portion of the lung. The second coil may include the first bioabsorbable material that is covered with a second bioabsorbable material. The second coil may begin to degenerate after the first coil ceases to degenerate.

In particular aspects, the method includes positioning a first valve adjacent a second target within a patient. The first valve may have a closed configuration and an open configuration. In the closed configuration, air may be permitted to exit a second portion of a lung and is prevented from entering the second portion of the lung. In the open configuration, air may be permitted to enter and exit the second portion of the lung. The method may include positioning a second valve adjacent a third target within the lung. The second valve may have a closed configuration in which air is permitted to exit a third portion of a lung and prevented from entering the third portion of the lung and an open configuration in which air is permitted to enter and exit the third portion of the lung.

In certain aspects, the method may include transitioning the first valve from the open configuration to the closed configuration from external of the patient. The method may include accessing breathing of the patient over an extended amount of time with the first valve in the closed configuration. The method may include returning the first valve to the open configuration after accessing breathing of the patient from external of the patient. Positioning the first coil adjacent the first target may include passing the first coil through the first valve when the first valve is in the open configuration.

In aspects, the method includes applying energy to the first coil from external of the patient to at least one of initiate degeneration of the first coil, cease degeneration of the first coil, and/or accelerate degeneration of the first coil. The method may include applying energy to the first coil to transition the coil from a linear configuration to a coiled configuration from external of the patient.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
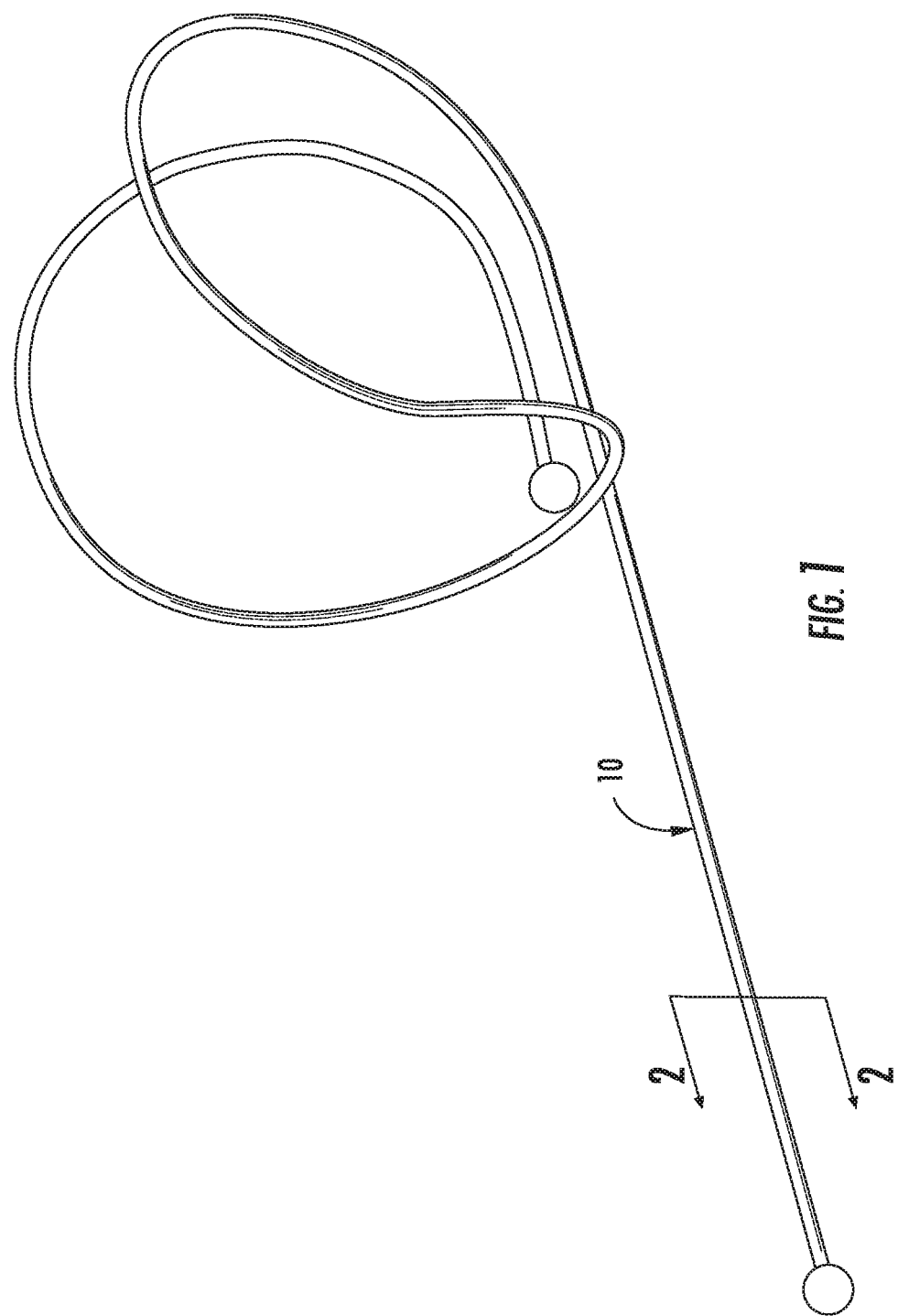
FIG. 1 is a perspective view of a coil provided in accordance with the present disclosure in a coiled configuration.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

This disclosure relates generally to biodegradable coils or valves which are configured to be disposed within a lung of a patient. The coils are configured to be inserted in a linear configuration and transition to a coiled configuration when positioned within a lung such that an airway of the lung is folded to deactivate a portion of the lung beyond the coil. The coil includes a first bioabsorbable material which is configured to cause a local inflammatory response to seal the portion of the lung beyond the coil as the coil degrades. After the coil fully degrades, the portion of the lung is deactivated with the coil being fully degraded and absorbed by the body. The deactivated portion of the lung shrinks as a result of air trapped within the deactivated portion being absorbed.

Figure 2:
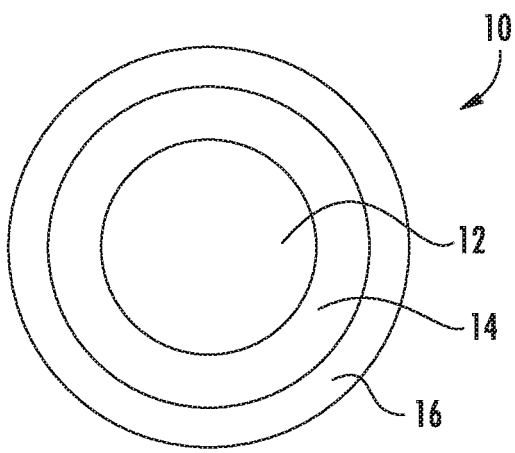
FIG. 2 is a cross-sectional view taken along the section line 2-2 of FIG. 1.
Figure 3:
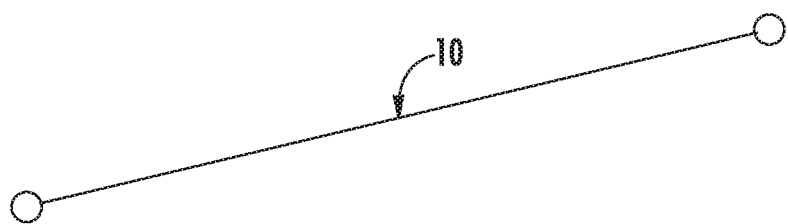
FIG. 3 is a perspective view of the coil of FIG. 1 in a linear configuration.

With reference to FIGS. 1-3, a coil 10 is disclosed in accordance with the present disclosure. As shown in FIG. 2, the coil 10 may be formed of multiple materials. For example, the coil 10 may include a core material 12, a first coating 14, and a second coating 16. The core material 12 is formed of a biodegradable shape-memory material that has a linear configuration (FIG. 3) and a coiled configuration (FIG. 1). Suitable materials for the core material 12 may include, but are not limited to, magnesium; calcium phosphate; zinc; zirconium; titanium compounds; starches including polyglycolic acid and polylactic acid; nitnol; alloys of copper, zinc, and aluminum; and alloys of iron, manganese, and silicon with gold. As detailed below, the core material 12 is configured to be inserted into an airway in the linear configuration and to transition to the coiled configuration after insertion to fold the airway onto itself. The core material 12 may be self-biased towards the coiled configuration or may transition to the coiled configuration when reaching a particular temperature. Additionally or alternatively, the coil 10 may be formed of a shape-memory material which maintains the linear configuration until the material is exposed to a particular energy which initiates a transformation of the shape-memory material from the linear configuration to the coiled configuration. For example, the shape-memory material may be initiate transformation when exposed to a wavelength of light, a magnetic field, an electrical field, and/or a temperature. Similar coils formed of shape memory alloys, which are not biodegradable, are currently produced by PneumRx® as the PneumRx® Coil System.

The core material 12 may be formed entirely from and/or be impregnated with a first bioabsorbable material that is configured to degenerate within the within the lung to induce a local inflammatory process such that fibrosis and scarring occurs in tissue. This fibrosis and scarring may seal or close off the airway within the lung which may result in partial atelectasis. The first bioabsorbable material degenerates over a predetermined amount of time such that a duration of the local inflammatory process ceases after the predetermined amount of time, i.e., when the first bioabsorbable material is absorbed. After degeneration of the first bioabsorbable material is completed, the lung can heal as a result of the cessation of the local inflammatory process. It will be appreciated that the core material 12 fully degrades such that the core material is also absorbed such that no foreign material remains within the lung. It will be appreciated that foreign materials within the lungs may increase infections and/or cause inflammation which can result in increased bleeding as a result of the foreign materials being in continued and ongoing proximity to the vasculature. Further, the pulsatile nature of vasculator may impart friction with foreign materials within the lungs. As a result, the foreign material may reduce or prevent healing within the lung until the foreign material no longer remains within the lung.

Referring back to FIG. 2, the coil 10 may include a first coating 14 formed over the core material 12. The first coating 14 may be formed of the first bioabsorbable material such that as the coil 10 is positioned within the lung, the first bioabsorbable material begins to degenerate and create the local inflammatory process as detailed above. When the first bioabsorbable material fully degenerates, the core material 12 is exposed such that the biodegradable shape-memory material begins to degrade after the local inflammatory process is completed. This sequential degeneration of the first coating 14 and degrading of the core material 12 may permit the lung to seal an airway while being folded and then, after the airway is sealed, the core material 12 fully degrades to eliminate foreign material from the lung. In such embodiments, the core material 12 may be formed entirely of the shape memory material or may also be impregnated with the first bioabsorbable material. Alternatively, the core material 12 may be impregnated with a different bioabsorbable material which is configured to promote healing of lung tissue after the local inflammatory process is completed. It is contemplated that the core material 12 may be impregnated with an anti-inflammatory material to reduce an inflammatory response as the coil 10 degrades.

In some embodiments, the first coating 14 is formed of a second bioabsorbable material which is absorbed over a predetermined amount of time without causing a local inflammatory process. In such embodiments, the core material 12 is impregnated with the first bioabsorbable material such that after a predetermine amount of time the first coating 14 degenerates and the core material 12 is exposed to begin the local inflammatory process.

Continuing to refer to FIG. 2, the coil 10 may include a second coating 16 over the first coating. In such embodiments, the second coating 16 is formed of the second bioabsorbable material, the first coating 14 is formed of the first bioabsorbable material, and the core material 12 may be formed entirely of the biodegradable material such that the local inflammatory process is delayed after placement within the lung until after the second bioabsorbable material degenerates to expose the first bioabsorbable material. It is contemplated that the core material 12 may be impregnated with the first bioabsorbable material to continue the inflammatory process and/or may be impregnated with the different bioabsorbable material to promote healing of the lung tissue as the local inflammatory process is completed. Additionally or alternatively, the second coating 16 may also have antimicrobial properties.

As detailed below, the coil 10 may be used to create fibrosis and/or scarring of tissue surrounding the coil 10 such that atelectasis occurs in a portion of a lung to deactivate a portion of the lung as detailed below. Specifically, as a portion of the lung is deactivated, the alveoli of the portion of the lung cease to receive air as the patient inhales and the air trapped within the deactivated portion of the lung is absorbed such that the deactivated portion of the lung shrinks. The shrinking of the deactivated portions of the lung may allow healthy portions of the lung to operate more freely and/or shift to areas previously containing the deactivated portions of the lung. It will be appreciated that the deactivated portions of the lung may be previously identified as diseased portions of the lung. Deactivating and/or shrinking diseased portions of the lung may increase the efficiency of the healthy portions of the lung.

Figure 4:
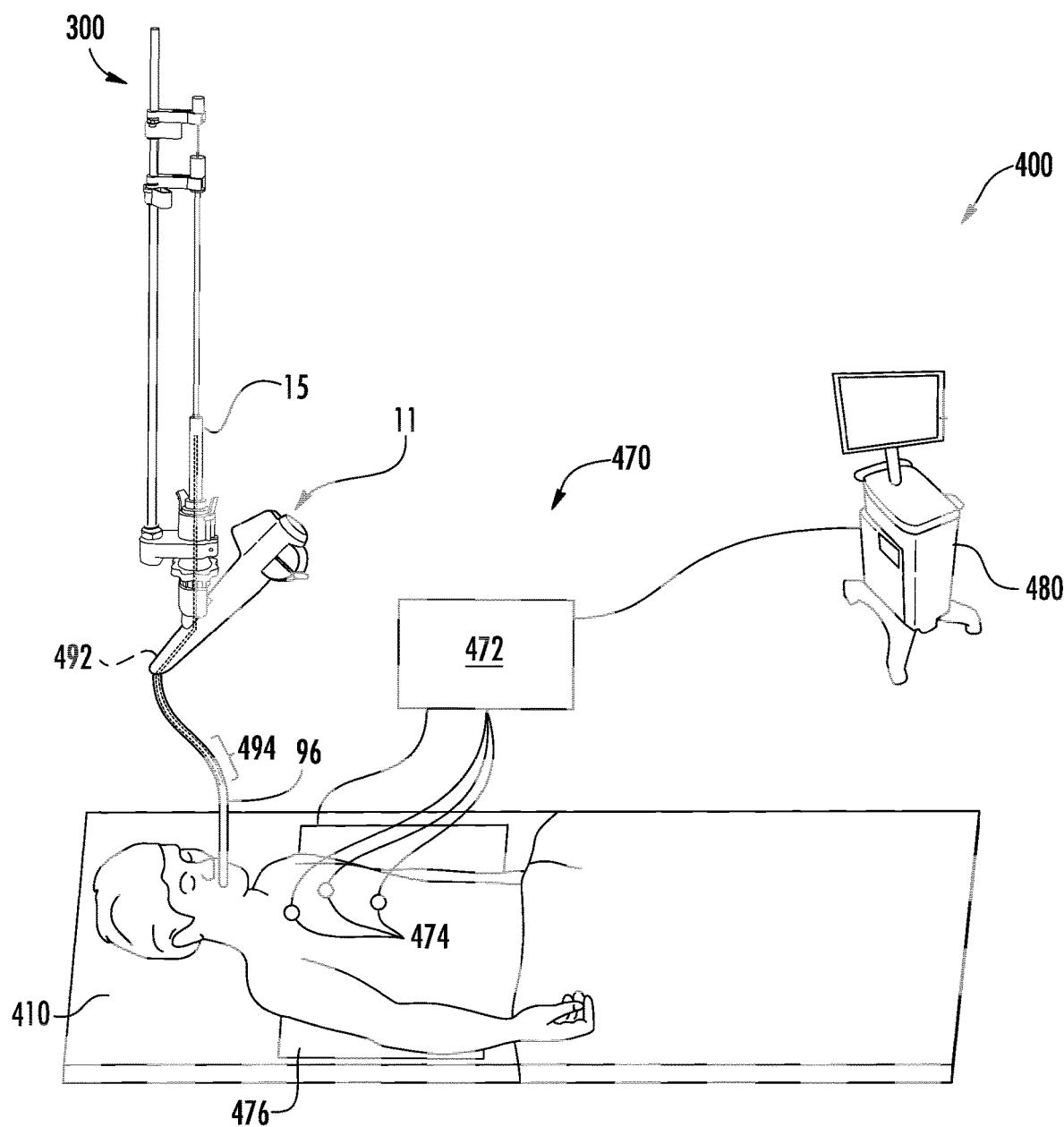
FIG. 4 is a perspective view of an exemplary surgical system including a rail system and an extended working channel in accordance with the present disclosure for use on a patient.
Figure 5:
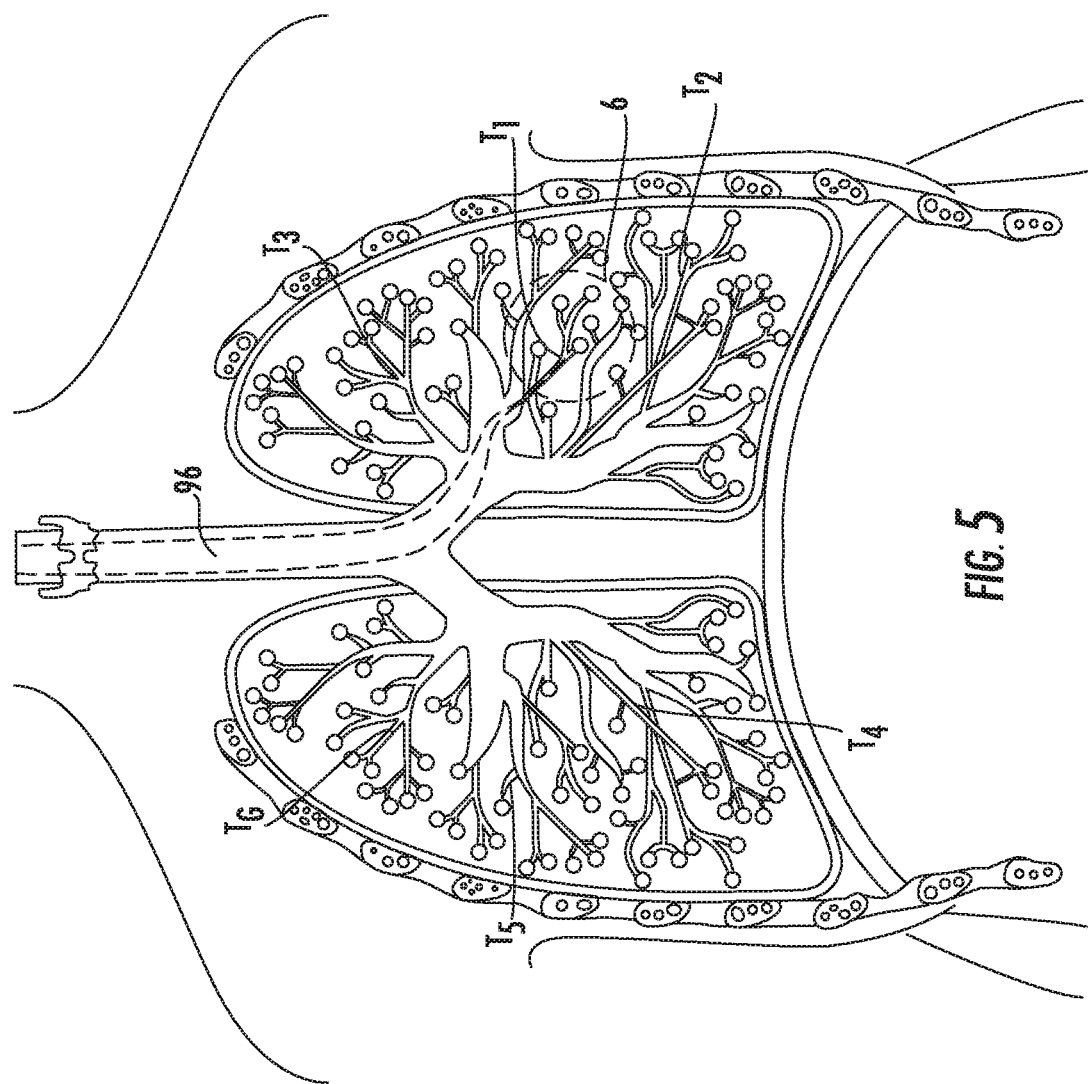
FIG. 5 is a schematic view of the extended working channel of FIG. 4 positioned adjacent a first target within lungs of the patient of FIG. 4.

Referring now to FIGS. 4 and 5, an electromagnetic navigation (EMN) system 400 is used to position the coil 10 within a lung of a patient. Specifically, the EMN system 400 is used to position an extended working channel (EWC) 96 within a lung of a patient such that the coil 10 can be passed through the EWC 96 to a target, e.g., first target $T_1$, within the lung. One such EMN system is the ELECTROMAGNETIC NAVIGATION BRONCHOSCOPY® system currently sold by Medtronic PLC. Among other tasks that may be performed using the EMN system 400 are planning a pathway to target tissue, navigating a catheter guide assembly to the target tissue, deploying an instrument adjacent targets to treat or capture the target tissue, and digitally marking the location of one or more targets in a data file related to the planned pathway.

The EMN system 400 generally includes an operating table 410 configured to support a patient; a bronchoscope 11 configured for insertion through the patient's mouth and/or nose into the patient's airways; a tracking system 470 including a tracking module 472, a plurality of reference sensors 474, an electromagnetic field generator 476; and a workstation 480 including software and/or hardware used to facilitate pathway planning, identification of target tissue, navigation to targets, and digitally marking the target areas or biopsy location. The bronchoscope 11 may include a telescopic handle 15 that is configured to receive catheters or surgical instruments therethrough.

A locatable guide (LG) catheter 492, including an electromagnetic (EM) sensor 494, is inserted into the telescopic handle 15, and may be connected to a rail system 300. Upon insertion into the telescopic handle 15, the LG catheter 492 enters the EWC 96 and is locked into position such that the sensor 494 is positioned slightly beyond the distal end 96a of the EWC 96 during placement of the EWC 96. The location of the EM sensor 494, and thus the distal end 96a of the EWC 96, within an electromagnetic field generated by the electromagnetic field generator 476 can be derived by the tracking module 472 and the workstation 480. During insertion and placement of the distal end 96a of the EWC 96, the telescopic EWC handle 15 and the LG catheter 492 inserted therein can be manipulated by rotation and compression to steer and position the LG catheter 492. An example of a similar catheter guide assembly is currently marketed and sold by Medtronic PLC under the name EDGE™ Procedure Kits. For a more detailed description of the use of the catheter guide assembly reference is made to commonly-owned U.S. Patent Publication No. 2016/0000302, the entire contents of which are hereby incorporated by reference.

Once the LG catheter 492 and EM Sensor 494 are navigated to a target within the patient, e.g., first target $T_1$, the LG catheter 492 is removed from the EWC 96 with the bronchoscope 11 and the distal end 96a of the EWC 96 remaining positioned adjacent the target. In addition, a sensor-based hollow-tipped catheter can be used to accomplish the same thing without the need to remove the LG catheter 492.

With continued reference to FIG. 5, the distal end 96a of the EWC 96 is positioned adjacent a first target $T_1$ within a lung. As shown, the first target $T_1$ is within a bronchial tube; however, the target may be alveoli or other tissue of a lung. With the EWC 96 positioned adjacent the first target $T_1$, a coil 10 can be passed through the EWC 96 and positioned at the first target $T_1$ in the linear configuration.

Figure 6:
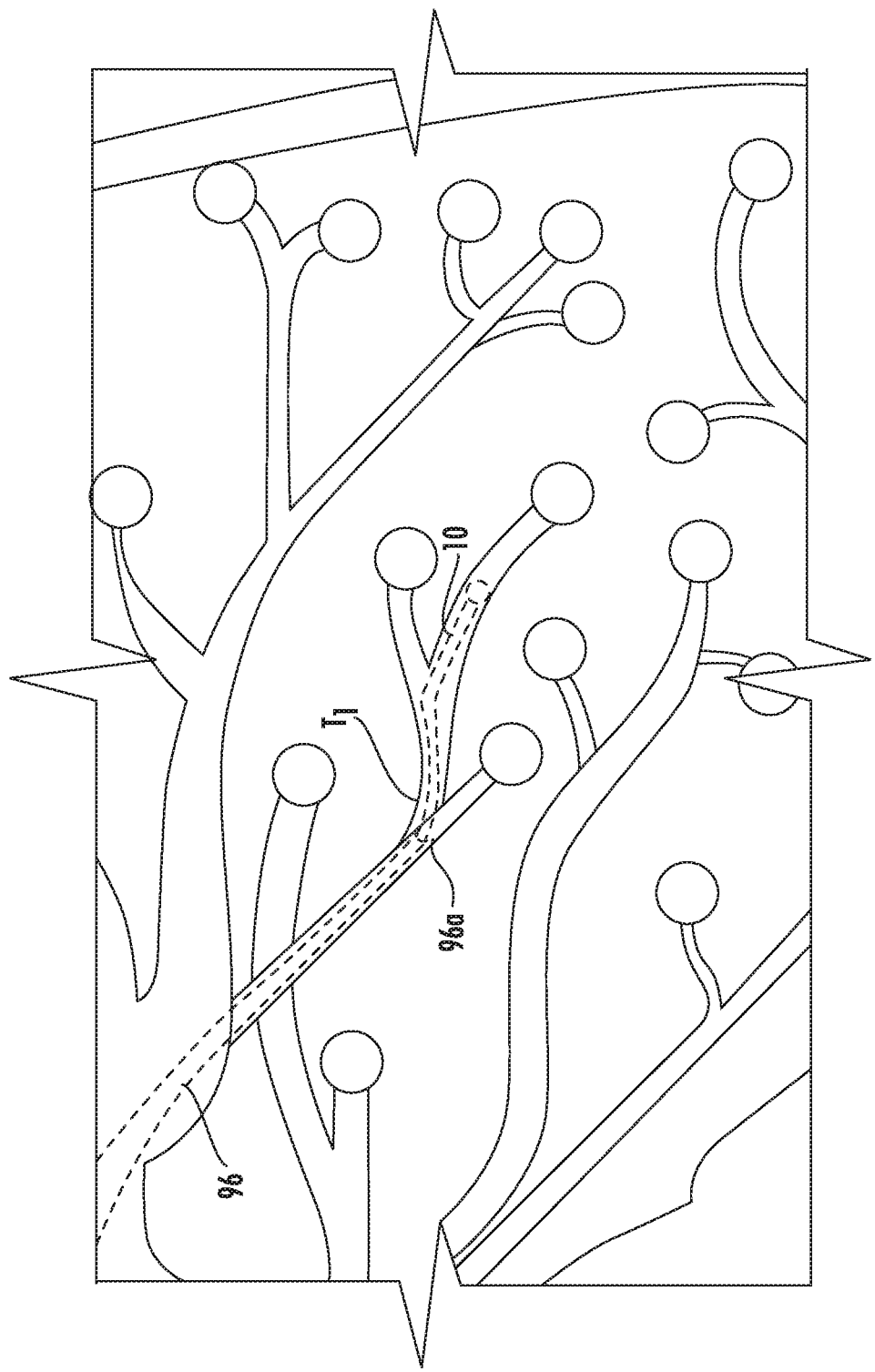
FIG. 6 is an enlarged view of the indicated area of detail of FIG. 5 illustrating a coil positioned at the first target in a linear configuration.
Figure 7:
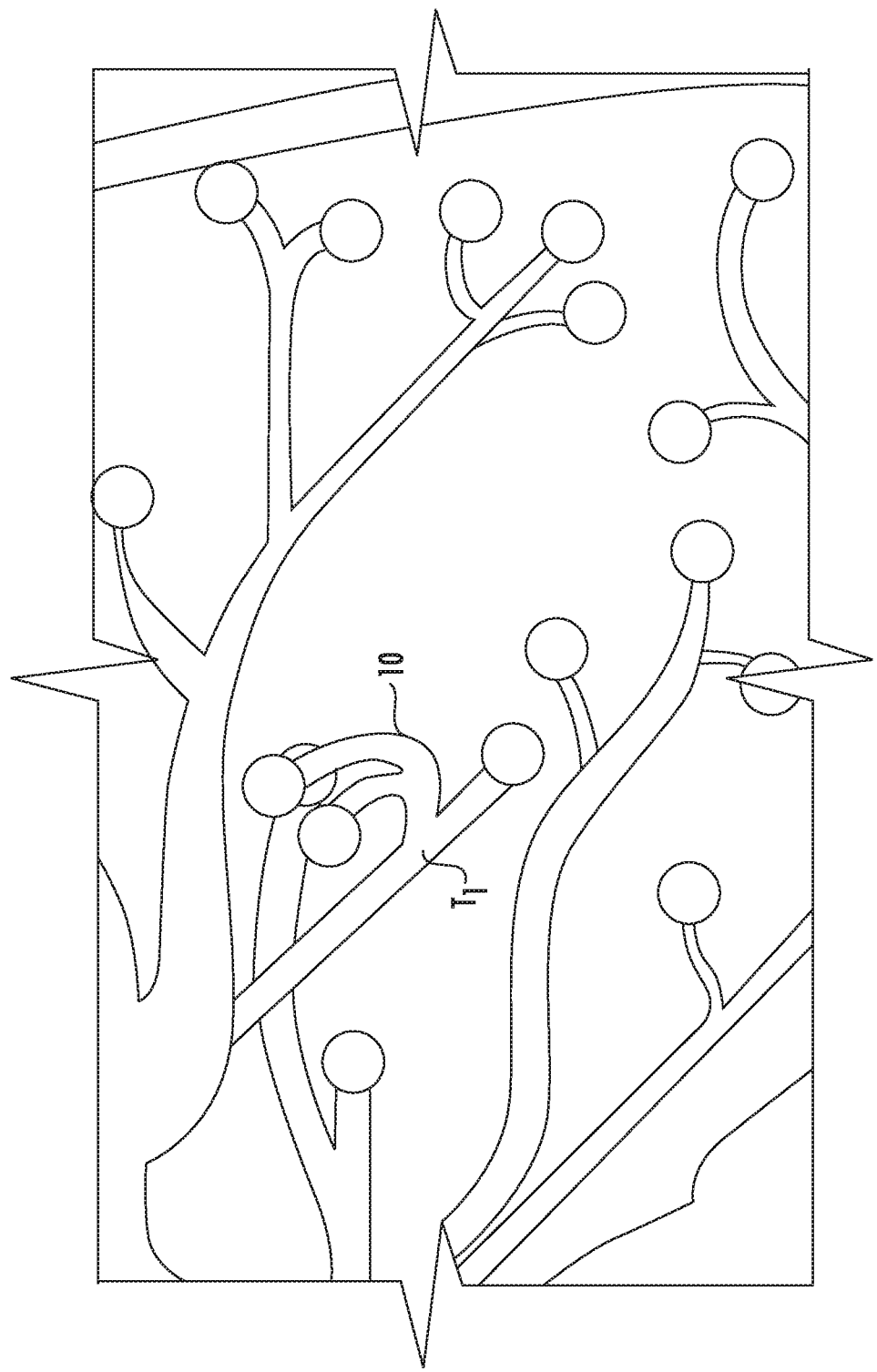
FIG. 7 is a schematic view of the coil of FIG. 6 in a coiled configuration to deactivate a portion of the lung.
Figure 8:
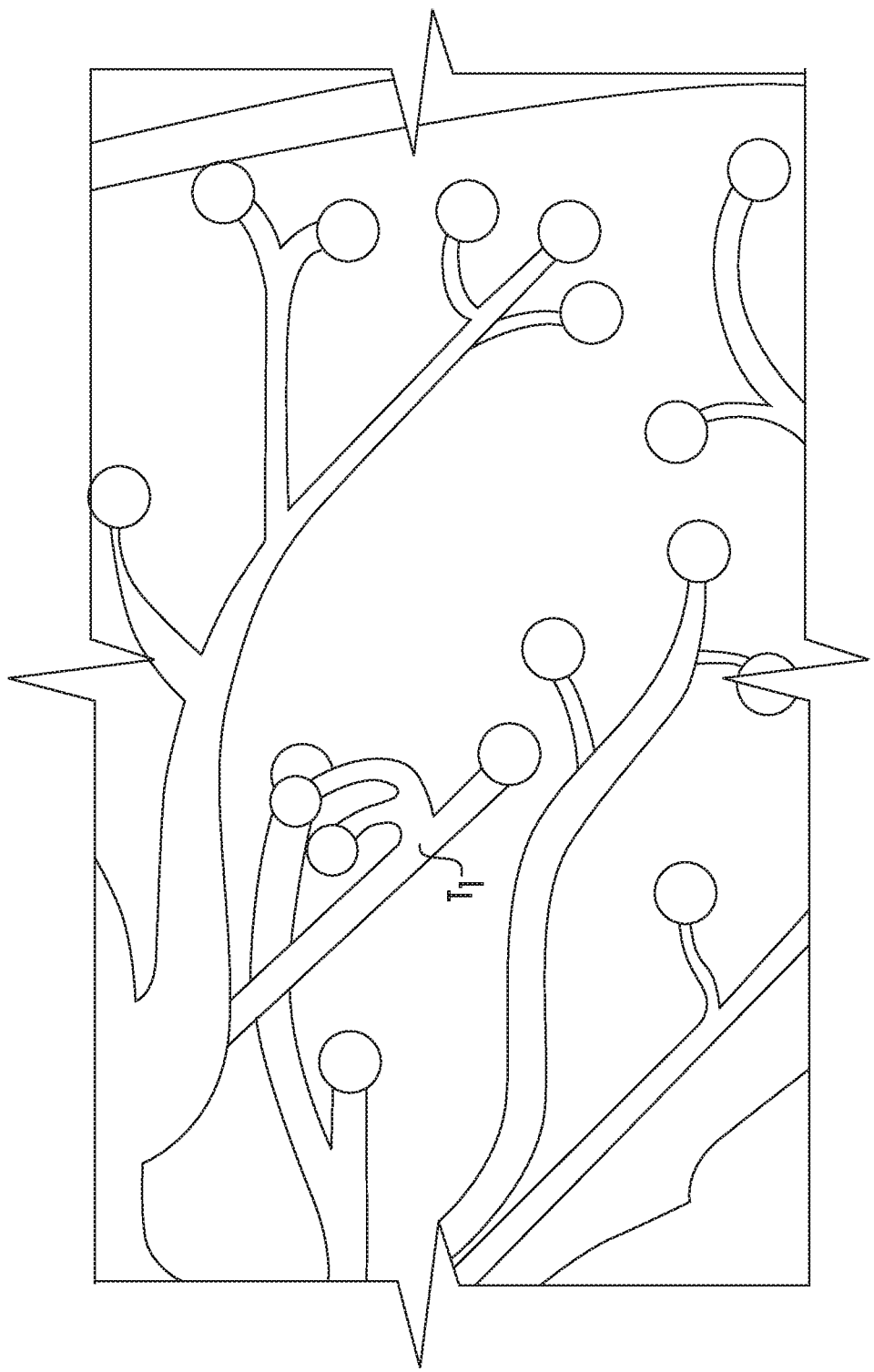
FIG. 8 is a schematic view of the deactivated portion of the lung after the coil fully degrades.

With reference to FIGS. 6-8, the deployment of the coil 10 is described in accordance with the present disclosure. As the coil 10 is positioned at the first target $T_1$, the coil 10 is in the linear configuration and extends through an airway of the lung. The coil 10 may be deployed by extending a sleeve (not shown) through the airway and then withdrawing the sleeve. The sleeve may maintain the coil 10 in the linear configuration such that as the sleeve is withdrawn, the coil 10 transitions to the coiled configuration as shown in FIG. 7.

Additionally or alternatively, the coil 10 may be formed of a shape-memory material which maintains the linear configuration until the material is exposed to a particular energy which initiates a transformation of the shape-memory material from the linear configuration to the coiled configuration. For example, the shape-memory material may be initiate transformation when exposed to a wavelength of light, a magnetic field, an electrical field, and/or a temperature.

With continued reference to FIG. 7, as the coil 10 transitions to the coiled configuration, the coil 10 folds the airway, in which the coil 10 is positioned, about itself such that the airway is closed and the portion of the lung beyond the first target $T_1$ is deactivated. When the coil 10 is in the coiled configuration, the coil 10 degenerates to cause a local inflammatory process at the first target $T_1$. The local inflammatory process causes fibrosis and/or scaring to form at the first target $T_1$ which forms a seal at the first target $T_1$ and deactivates the portion of the lung beyond the first target $T_1$. As the seal is formed at the first target $T_1$, air trapped in the portion of the lung beyond the first target $T_1$ escapes past the first target $T_1$ and/or is absorbed such that the deactivated portion of the lung shrinks. This shrinking allows for other portions of the lung to shift into the area previously occupied by the deactivated portion of the lung.

Referring to FIG. 8, after a predetermined period of time, the coil 10 fully degrades such that the coil 10 is fully absorbed and the deactivated portion of the lung is sealed by the fibrosis and scarring created by the local inflammatory process. The fibrosis and scarring maintains the seal of the deactivated portion of the lung in the absence of any foreign material, e.g., the coil 10.

Figure 9:
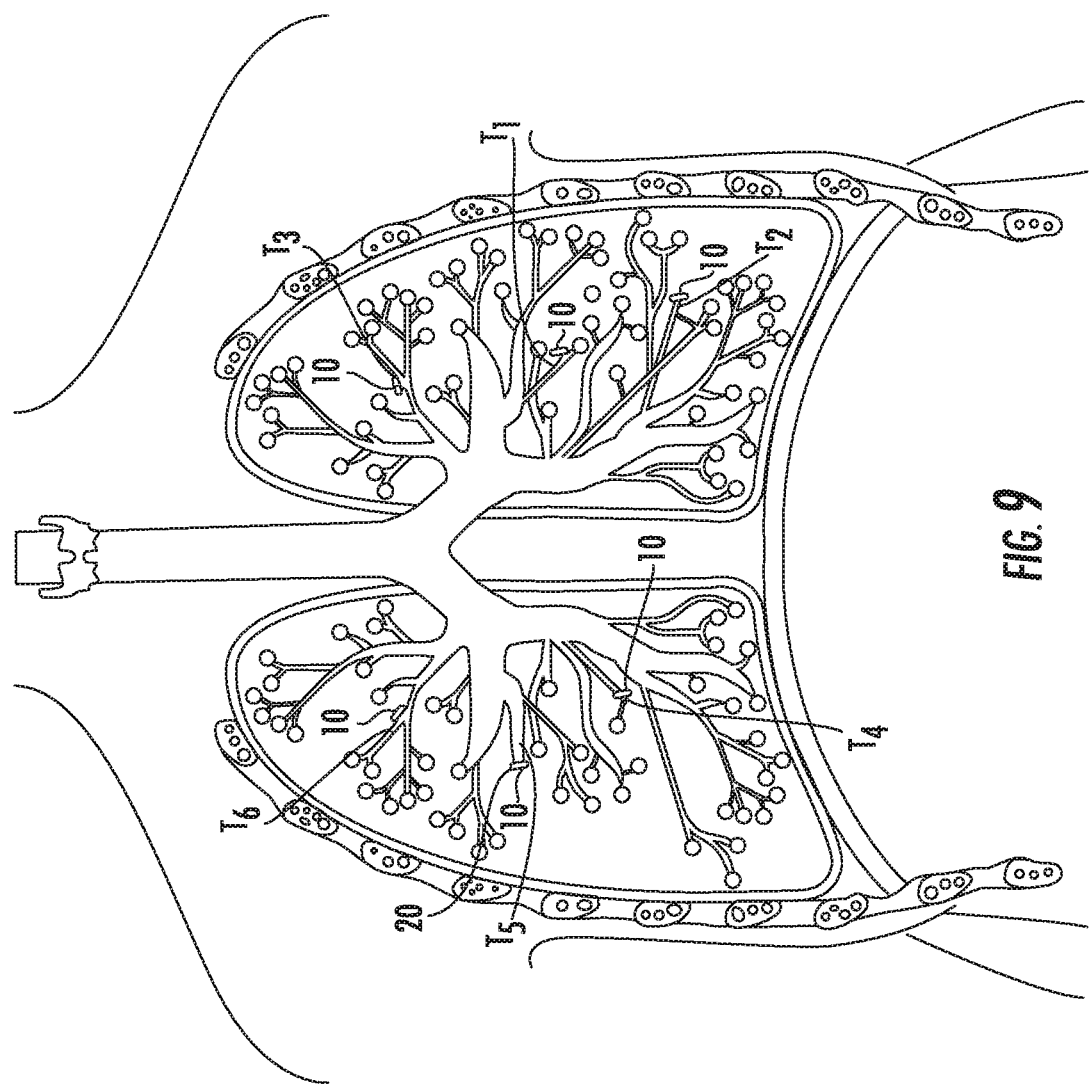
FIG. 9 is a schematic view of the lungs of FIG. 5 with portions of the lungs deactivated by coils.

As shown in FIG. 9, multiple coils 10 may be positioned at multiple targets, e.g., $T_1$, $T_2$, $T_3$, $T_4$, $T_5$, $T_6$, within the lung to deactivate portions of the lung beyond each of the multiple targets. It will be appreciated that each of the deactivated portions of the lung may have been previously identified as diseased.

Each of the coils 10 may be formed of only the core material 12 (FIG. 2) impregnated with the first bioabsorbable material. In these embodiments, when the coils 10 are positioned at the respective targets within the lung, the local inflammatory process begins at each of the targets. Alternatively, one or more of the coils 10 may include the first and/or second coatings 14, 16 (FIG. 2) having a bioabsorbable material which degenerates over a predetermined amount of time, without inducing a local inflammatory process, such that the bioabsorbable material of the coil, which is configured to induce a local inflammatory process, is exposed after the predetermined amount of time. The predetermined amount of time may be the same for each of the coils 10 or may be different for each of the coils 10 to stagger degeneration of each of the coils 10, and thus, each of the local inflammatory processes. Staggering the degeneration of the coils 10 may be beneficial to reduce the amount of inflammation at any given moment within the lungs of a patient as a result of the degeneration of the coils 10. Reducing the amount of inflammation at any given moment may reduce trauma to a patient and improve treatment outcomes. It is contemplated that the core, e.g., core 12, of each of the coils 10 may be impregnated with an anti-inflammatory material such that after the local inflammatory process is complete at each coil 10, the anti-inflammatory material reduces the local inflammatory response as the coil 10 degrades. It will be appreciated that the reduction in local inflammatory response during degradation of the coil 10 may reduce the over all inflammation within the lungs of a patient as coatings 12, 14 of other coils 10 within the lungs degenerate. The predetermined amount of time of each of the coils 10 may be in a range of about one minute to about three months.

Additionally or alternatively, degeneration of the coil 10 may be activated non-invasively after the coil 10 is positioned at a respective target. For example, the coil 10 may be activated by a magnetic field applied to the coil 10 from a point external to the patient. Additionally or alternatively, the degeneration of the coil 10 may be accelerated by delivering energy to the coil 10. For example, heat may be applied to the coil 10 to accelerate degeneration or absorption of the coil 10. Heat may be applied from a point internal to or external of the patient. For example, converging energy beams, e.g., infra-red beams, originating external of the patient may harmlessly pass through tissue and converge on or adjacent the coil 10 to apply heat to the coil 10.

With reference to FIGS. 4-9, a method of altering lung volume is disclosed in accordance with the present disclosure. Initially, the EMN system 400 is used to position the distal end 96a of the EWC 96 adjacent a first target $T_1$ within a lung of a patient. A coil 10 is then passed through the EWC 96 and positioned at the first target $T_1$. The distal end 96a of the EWC 96 is then repositioned adjacent the second target $T_2$ to position another coil 10 at the second target $T_2$. This is repeated until a coil 10 is positioned at each target within the lung.

As detailed above, each coil 10 may be self-biased such that when the coil 10 is positioned at the respective target, the respective coil 10 transitions from the linear configuration to the coiled configuration to deactivate the portion of the lung beyond the respective target. Alternatively, after all the coils 10 are positioned at a respective target, energy may be delivered to the coil 10 such that the coil 10 transitions from the linear configuration to the coiled configuration. It is contemplated that this transition from the linear configuration to the coiled configuration may also initiate degeneration of the coil 10 by exposing a bioabsorbable material of the coil 10. Energy may be delivered to each of the coils 10 individually or simultaneously. By selectively delivering energy to particular coils 10, a clinician can observe the volume reduction and/or shifting within the lung before delivering energy to a subsequent coil 10 to deactivate another portion of the lung.

Additionally or alternatively, energy may be delivered to one or more of the coils 10 to return one or more of the coils 10 to the linear configuration from the coiled configuration if a clinician desires to reactivate a previously deactivated portion of the lung. The delivery of energy may also terminate degeneration of the coil 10. For example, the delivery of energy may instantly degrade the coil 10. By accessing a patient with varying portions of the lungs activated and deactivated, a clinician can determine which portions of the lungs of a patient to permanently deactivate.

With particular reference to FIG. 9, the EMN system 400 (FIG. 4), can be used to position one or more valves 20 within the lung. The valves 20 may be positioned at a respective target, e.g., target $T_5$. It is also contemplated that one or more coils 10 may be disposed beyond a respective valve 20.

Each of the valves 20 has a closed configuration in which air is permitted to pass through in a first direction and prevented from passing through the valve 20 in a second opposite direction. As shown, the valve 20 is oriented at the fifth target $T_5$ such that in the closed configuration air is prevented from entering a portion of a lung through the valve 20 and air is allowed to exit or escape the portion of the lung through the valve 20 such that atelectasis occurs beyond the valve 20 and the volume of the portion of the lung is reduced when the valve 20 is in the closed configuration. The valve 20 may be a duckbill valve.

The valve 20 may also have an open configuration in which air is permitted to freely pass through the valve 20 in both directions. The valve 20 may be secured at the fifth target $T_5$ in the open configuration and be controlled to transition to the closed configuration by external application of energy. For example, a magnetic field may be generated external to the patient such that the valve 20 transitions between the open and closed configurations. In some embodiments, the valve 20 is coated with a first bioabsorbable material that is configured to induce an inflammatory response in tissue adjacent the valve 20. In particular embodiments, the valve 20 is coated with a second bioabsorbable material that dissolves during a predetermined amount of time, without inducing a local inflammatory process, such that a first bioabsorbable material, which is configured to induce a local inflammatory process, is exposed after the predetermined amount of time.

After a valve 20 is positioned at a respective target, the valves 20 may be externally controlled to alter the volume of the lungs. For example, magnetic fields generated external to the patient may transition a valve 20 between closed and open configurations. By opening and closing the valves 20, a clinician can selectively and reversibly deactivate and activate portions of a patient's lungs and access the patient with an altered lung volume. By accessing a patient with varying portions of the lungs activated and deactivated, a clinician can identify which portions of the lungs of a patient to permanently deactivate.

With the portions of the lungs of a patient identified, the clinician can leave particular valves 20 in the closed configuration and/or activate a coil 10 positioned adjacent the valve 20, in front of or beyond the valve 20, to permanently deactivate the portion of the lung. Additionally or alternatively, one or more plugs (not explicitly shown) can be used in place of a closed valve to permanently deactivate a portion of the lung.

It will be appreciated that by positioning multiple coils 10 and/or valves 20 during a single procedure, trauma to a patient can be reduced by not requiring multiple procedures. In addition, by allowing a clinician to activate and deactivate portions of lungs of a patient, that a clinician may be able to access the effects of deactivating portions of the lungs of a patient before permanently deactivating portions of the lungs. Each of the above benefits, when taken alone or in combination, may improve patient outcomes by reducing time, costs, and trauma associated with altering lung volume procedures. Additionally, reducing the duration of time that a fixed foreign body is adjacent to the vasculature can also reduce the likelihood of substantive bleeding.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. A medical device for altering lung volume, the medical device comprising:
    a core formed of a biodegradable material and configured to be inserted into an airway of a patient's lung in a linear configuration and to transition to a coiled configuration after insertion to fold the airway onto itself, wherein:
        the core is configured to transition to the coiled configuration upon exposure of the core to a magnetic field after insertion;
        the core degenerates upon insertion into the airway of the patient; and
        the degeneration of the core is configured to accelerate upon a non-invasive application of energy to the core originating from an energy source external of the patient such that the applied energy passes through tissue of the patient to heat the core; and
    a first bioabsorbable material different from the biodegradable material, the first bioabsorbable material configured to cause a local inflammatory response to deactivate a portion of the lung as the first bioabsorbable material is absorbed into the lung.

2. The medical device according to claim 1, wherein the first bioabsorbable material is a coating disposed over the core.

3. The medical device according to claim 1, wherein the first bioabsorbable material is impregnated in the biodegradable material of the core, and the core is coated with a second bioabsorbable material configured to dissolve after a predetermined amount of time.

4. The medical device according to claim 1, further comprising a second bioabsorbable material coating the first bioabsorbable material, the second bioabsorbable material configured to dissolve after a predetermined amount of time.

5. The medical device according to claim 1, wherein the biodegradable material is a shape-memory material configured to transition from the linear configuration to the coiled configuration when positioned adjacent a target within a patient and exposed to energy that initiates the transition.

6. The medical device according to claim 1, wherein the core is configured to cease degeneration in response to energy applied to the core from outside of the patient.

7. A coil for altering lung volume, the coil comprising:
    a core configured to be inserted into an airway of a patient's lung in a linear configuration, the core formed of a biodegradable shape-memory material and configured to transition from the linear configuration to a coiled configuration after insertion to fold the airway onto itself, wherein:
        the core degenerates upon insertion into the airway of the patient and the degeneration of the core is configured to accelerate upon a non-invasive application of energy to the core originating from an energy source external of the patient such that the applied energy passes through tissue of the patient to heat the core; and
    a bioabsorbable coating different from the biodegradable shape-memory material, the bioabsorbable coating applied to the core and configured to degrade prior to a degrading of the biodegradable shape-memory material to cause a local inflammatory response within the lung and subsequently expose the core such that the degrading of the biodegradable shape-memory material is initiated subsequent to the causing of the local inflammatory response within the lung.

8. The coil according to claim 7, wherein the core is self-biased to the coiled configuration.

9. The coil according to claim 7, wherein the core transitions from the linear configuration to the coiled configuration at a threshold temperature of the core.

10. The coil according to claim 7, wherein the core transitions from the linear configuration to the coiled configuration when exposed to a magnetic field after insertion.

11. A coil for altering lung volume, the coil comprising:
a core configured to be inserted into an airway of a patient's lung in a linear configuration, the core formed of a biodegradable shape-memory material and configured to transition from the linear configuration to a coiled configuration after insertion to fold the airway onto itself, wherein:
the core degenerates upon insertion into the airway of the patient and
the degeneration of the core is configured to accelerate upon a non-invasive application of energy to the core originating from an energy source external of the patient such that the applied energy passes through tissue of the patient to heat the core;
a first bioabsorbable coating different from the biodegradable shape-memory material, the first bioabsorbable coating applied to the core and configured to degrade prior to a degrading of the biodegradable shape-memory material to cause a local inflammatory response within the lung and subsequently expose the core such that the degrading of the biodegradable shape-memory material is initiated subsequent to the causing of the local inflammatory response within the lung; and
a second bioabsorbable coating different from the first bioabsorbable coating and the biodegradable shape-memory material, the second bioabsorbable coating applied to the first bioabsorbable coating and configured to degrade prior to the degrading of the first bioabsorbable coating to expose the first bioabsorbable coating such that the degrading of the first bioabsorbable coating and the causing of the local inflammatory response within the lung are initiated subsequent to the degrading of the second bioabsorbable coating.

12. The coil according to claim 11, wherein the core is self-biased to the coiled configuration.

13. The coil according to claim 11, wherein the core transitions from the linear configuration to the coiled configuration at a threshold temperature of the core.

14. The coil according to claim 11, wherein the core transitions from the linear configuration to the coiled configuration when exposed to a magnetic field or electrical field after insertion.

* * * * *